United States Patent [19]

Mower et al.

[11] Patent Number: 5,476,497
[45] Date of Patent: Dec. 19, 1995

[54] OVAL ELECTRODE LEAD BODY

[75] Inventors: Morton M. Mower, Edina, Minn.; Seah Nisam, Oxshott, England

[73] Assignee: Ann Mirowski, Owings Mills, Md.

[21] Appl. No.: 290,113

[22] Filed: Aug. 15, 1994

Related U.S. Application Data

[63] Continuation of Ser. No. 51,316, Jun. 29, 1992, abandoned, which is a continuation-in-part of Ser. No. 638,511, Jan. 9, 1991, abandoned.

[51] Int. Cl.$^6$ ..................................................... A61N 1/05
[52] U.S. Cl. ............................................................ 607/122
[58] Field of Search ................................... 607/116, 119, 607/122

[56] References Cited

U.S. PATENT DOCUMENTS

| | | | |
|---|---|---|---|
| 3,333,045 | 7/1967 | Fisher et al. | 607/122 |
| 3,348,548 | 10/1967 | Chardack. | |
| 3,804,098 | 4/1974 | Friedman. | |
| 3,817,241 | 6/1974 | Grausz. | |
| 3,825,015 | 7/1974 | Berkovits. | |
| 3,949,757 | 4/1976 | Sabel. | |
| 4,458,677 | 7/1984 | McCorkle, Jr.. | |
| 4,481,953 | 11/1984 | Gold et al. | 607/122 |
| 4,567,901 | 2/1986 | Harris. | |
| 4,608,986 | 9/1986 | Beranek et al.. | |
| 4,627,439 | 12/1986 | Harris. | |
| 4,840,186 | 6/1989 | Lekholm et al.. | |

OTHER PUBLICATIONS

Fowler, N. O., ed., *Cardiac Arrhythmias Diagnosis and Treatment*, Harper & Row, Hagerstown, Md., 1977, p. 190.
Hill, W. E., et al., "Minimum Energy for Cardiac Pacing," *Clinical Physics And Physiological Measurement*, 9:1, 1988, abstract (pp. 41–46).
Schuchert, A. et al., "Steriod Eluting Pacemaker Electrodes–Improved Stimulation and Sensing Properties," *Deutsche Medizinische Wochenschrift*, 117:16, 1992, abstract (pp. 607–612).
Bardy, G. H., et al., "A Simplified, Single–Lead Unipolar Transvenous Cardioversion–Defibrillation System," *Circulation*, 88:2, abstract (pp. 543–547).
Saksena, S., et al., "Long–Term Multicenter Experience with a Second–Generation Implantable Pacemaker–Defibrillator in Patients with Malignant Ventricular Tachyarrhythmias," *Journal of the American College of Cardiology*, 19:3, 1992, abstract (pp. 490–499).
Saskena, S., et al., "Endocardial Pacing, Cardioversion and Defibrillation Using a Braided Endocardial Lead System", *American Journal of Cardiology*, 71:10, 1993, abstract (pp. 834–841).

*Primary Examiner*—William E. Kamm
*Assistant Examiner*—Scott M. Getzow
*Attorney, Agent, or Firm*—Keck, Mahin & Cate

[57] ABSTRACT

To prevent electrical conductors which connect a patient-implanted high energy electrode to a pulse generator from short circuiting at locations where a tubular lead body in which the conductors are contained encounters a sharp bend, the lead body has an oval cross section and the conductors are disposed on the major axis of the oval. This arrangement promotes preferential bending of the lead body about the major axis, rather than the minor axis of the oval body, tending to maintain the spacing between the conductors and thereby minimizing short circuits. The lead body can be resiliently compressed, however, for insertion into a patient in a cylindrical catheter of circular cross section.

19 Claims, 1 Drawing Sheet

OVAL ELECTRODE LEAD BODY

This is a continuation application of Ser. No. 08/051,316, filed on Jun. 29, 1992, now abandoned, which is a continuation-in-part application of Ser. No. 07/638,511, filed Jan. 9, 1991 now abandoned.

BACKGROUND OF THE INVENTION

The present invention relates to an electrode lead body for high energy systems using implantable electrodes, and specifically to an electrode lead body which maintains insulation and spacing between two conductors housed by the lead.

In implantable systems such as cardiac pacemakers and defibrillators, it is necessary to connect electrodes mounted on or about the heart with cardiac analysis, pacemaking, or defibrillating circuitry. The electrodes may be used for sensing or for delivering electrical energy to the heart. In procedures such as catheter ablation, a catheter lead is required to connect a source of electrical energy to a discharge electrode to be used proximate the myocardium. Regardless of the particular type or use of the electrodes, the lead which connects the electrodes with the circuitry will likely travel through tortuous and winding paths in the body.

In some applications, the lead must carry within it two or more insulated conductors for operatively connecting the electrodes with associated circuitry. A typical lead path begins at the point of connection to the pulse generator, just beneath the skin, and tunnels around the ribs into the thorax to a position in, on or about the heart. At relatively extreme bends in leads of circular cross section, such as may, for example, be encountered where a lead is bent around a patient's first rib, between the first rib and the clavicle, the insulated conductors could be pushed together by the bending forces. Although each conductor is insulated, the insulation is a thin layer of material so as to minimize the overall cross section of the lead, and at times the leads could be separated by only two thicknesses of insulation.

While thin layers of insulative material generally are suitable to separate conductors for sensing and pacing functions, such is not the case when high energy cardioverting or defibrillating pulses are being delivered. High energy discharges are capable of causing arcing between closely spaced conductors, even if the conductors are not touching one another and are insulated. While such arcing may occur in ablation procedures and is conceivable in pacing, it is a particular problem for high-energy applications like cardioversion and defibrillation. Typically, a pacemaker delivers energy levels on the order of microjoules through its lead assembly. A cardioverter or defibrillator, by contrast, delivers much higher energy levels, on the order of joules. Consequently, when delivering such higher-energy cardioverting electrical discharges, a short circuit can be created by arcing across the two insulated conductors if the conductors are forced toward another along the lead extreme bends.

Some pacing lead designs provide a solid lead body having small lumens therein for carrying conductors; see, for example, U.S. Pat. Nos. 3,348,548 to Chardack, 3,949,757 to Sabel and 4,608,986 to Bernek et al. Further, Fisher et al., U.S. Pat. No. 3,333,045, discloses a lead assembly for pacing in which one embodiment apparently includes an oval-shaped outer sheathing surrounding two insulated helical cables. Yet, none of these designs provides a sheathing for avoiding cable/insulation compression against adjoining cable/insulation at extreme bends, such protection being unnecessary for designs directed to lower-energy pacing applications. There thus remains the need for an improved high-energy lead design.

SUMMARY OF THE INVENTION

It is a primary object of the invention to provide a high energy electrode lead body for carrying at least two conductors and which decreases the possibility of short circuiting between the conductors at extreme bends in the lead.

It is another object of the invention to provide a high energy electrode lead body having a non-circular cross-sectional shape which promotes preferential bending of the lead body in a manner decreasing the possibility of short circuiting of the conductors, but which is sufficiently flexible or compressible so that it can adapt a substantially circular cross section to facilitate insertion into the body by conventional cylindrical introducing instruments of circular cross section.

Briefly stated, the invention provides a lead body, particularly for the purposes indicated, the lead body being of tubular form for receiving the at least two conductors and having an elongated, preferably oval, cross section. With a lead body having a cross section of oval shape, the conductors are spaced along the major axis of the lead body and the elongated shape of the lead body promotes bending along the major axis (rather than the minor axis) tending to retain the spacing between the conductors and thereby decreasing the possibility of short circuiting due to compressive forces urging together the individual conductors of the conductor/insulation pair when the lead is bent sharply.

The lead design according to the present invention may also be used in conjunction with lower-energy catheter ablation and pacing applications, but is particularly advantageous with high-energy applications such as cardioversion and defibrillation.

The above and other objects and advantages of the present invention will become more readily apparent when reference is made to the following description taken in conjunction with the accompanying drawings.

DESCRIPTION OF PREFERRED EMBODIMENT

Figure 1:
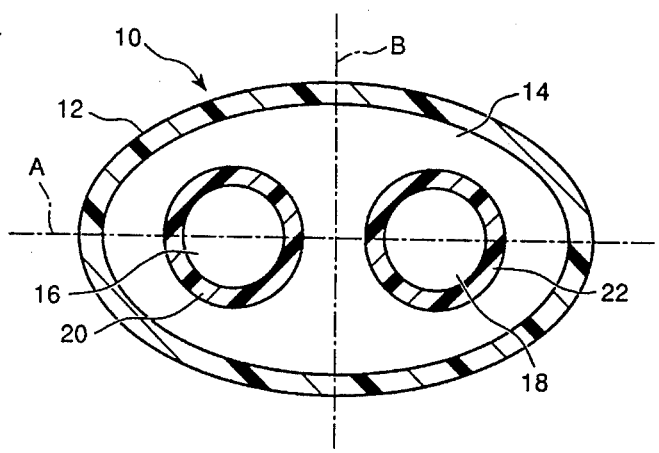
FIG. 1 is a cross-sectional view of an electrode lead body according to the present invention.

Referring to FIG. 1, an electrode lead body according to the present invention is shown in cross section at 10. The lead body 10 comprises an oval shaped wall or tube 12 made of insulative material of a type which is generally used for such applications, for example silastic or polyurethane. The wall 12 is preformed by extrusion or other known means to an oval shape in cross section to create an inner oval cavity 14. The oval-shaped wall has a major axis A and a minor axis B.

The lead body 10 contains and carries within it at least two insulated conductors 16 and 18, each being surrounded by insulative material 20 and 22, respectively. The insulated conductors naturally tend to align themselves along the major axis A. Typical dimensions for conductors and lead body to obtain suitable spacing between the conductors may, for example, be as follows:

|  | Typical | Range |
| --- | --- | --- |
| Diameter of Conductors: | 0.9 mm | 0.5–2.0 mm |
| Length of lead body (axis A): | 3.0 mm | 2.0–7.0 mm |
| Width of lead body (axis B): | 1.1 mm | 1.0–3.0 mm |

Figure 2:
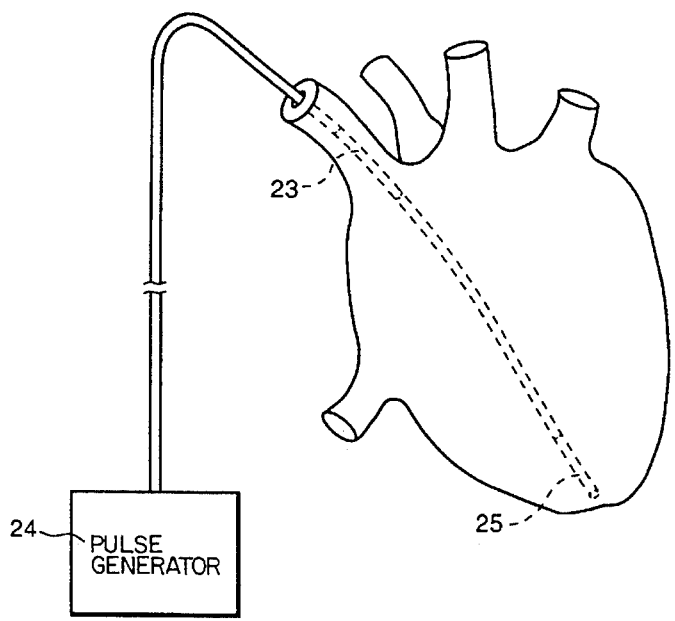
FIG. 2 is a schematic diagram illustrating the electrode lead body as used in a cardiac cardioverting or defibrillating system.

By providing a lead body of oval form and disposing the conductors along the major axis, the lead body will naturally tend to bend about the major axis and thereby tend to maintain the spacing between the conductors. Also, since the space between a patient=s first rib and the clavicle is somewhat narrow while being open laterally, the shape of this space makes the lead seek the desired orientation, when it is led through the space. Accordingly, when the lead body is used, for example, to effect high energy discharges to conductors 23 and 25 implanted in a patient's heart (FIG. 2) to deliver cardioverting or defibrillating pulses from a pulse generator 24, any sharp bend encountered by the lead in passing through the patient's body, should not tend to cause short circuiting of the conductors.

Figure 3:
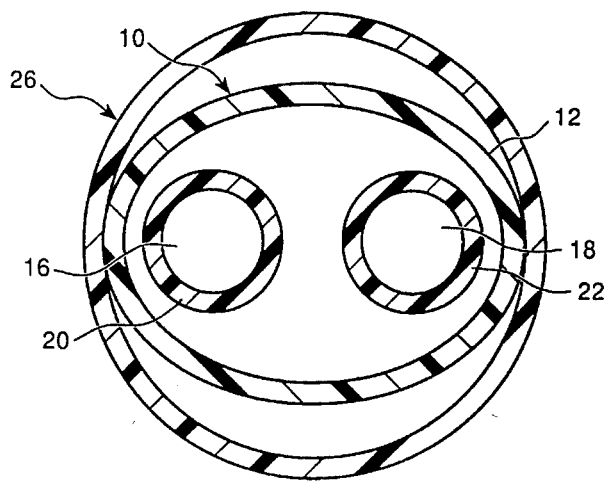
FIG. 3 is a cross-sectional view illustrating the oval electrode lead body in a compressed state when introduced through an insertion catheter into the body.

The lead body 10, however, is sufficiently flexible or compressible to allow insertion into a cylindrical catheter of circular cross section 26 as shown in FIG. 3, for insertion of the lead body into the patient.

While only a preferred embodiment of the invention has been described herein in detail, the invention is not limited thereby, and modifications can be made within the scope of the attached claims.

We claim:

1. A patient-implanted cardioversion electrode assembly connected to a pulse generator comprising:

electrical conductors adapted to extend from the pulse generator to the patient's heart, said electrical conductors of sufficient diameter to effectively carry a cardioversion current to the heart; and a tubular lead body of insulating material carrying said electrical conductors and having an elongated cross-sectional shape with a major axis and a minor axis at least at a location where the lead body is to be sharply bent, so as to promote preferential bending of the lead body about a major axis and to prevent the moving together and hence the short circuiting of the conductors, the conductors being free to move within said tubular lead body when the lead body is generally straight, but which are disposed in spaced relation on said major axis when and at locations where the lead body is sharply bent.

2. The electrode assembly of claim 1 wherein the lead body has an oval cross-sectional shape.

3. The electrode assembly of claim 1 wherein the lead body is readily resiliently compressed to form a cylindrical catheter of circular cross section for insertion into the patient.

4. The electrode assembly of claim 1 wherein the major axis width is of the approximate range from 2.0 to 7.0 mm, the minor axis width is of the approximate range from 1.0 to 3.0 mm, and each conductor diameter is of the approximate range from 0.5 to 2.0 mm.

5. An electrical lead for connecting a pulse generator to a patient-implanted electrode for delivering high-energy discharges to the heart of the patient, the lead preventing short circuiting between a pair of insulated electrical conductors in the event the lead is bent sharply, the lead comprising:

a tubular lead body of insulating material having an elongated cross section with a major axis and a minor axis, the lead body preferentially bending about the major axis; and at least two insulated conductors contained within the lead body and disposed in spaced relation along the major axis, without experiencing forces urging together the insulated conductors even at regions where the electrical lead is sharply bent, said insulated conductors having sufficient cross sectional area to carry current for cardioverting a heart.

6. The electrical lead of claim 5 wherein the lead body has an oval cross section.

7. A catheter electrode for association with a remote electrical energy source, and to be implanted within the body of a patient, said catheter electrode comprising at least two conductive cardioversion electrodes for residing in or about the heart of a patient, an electrical conductor associated with each of said conductive electrodes, each of said electrical conductors for carrying levels of current for cardioverting the heart, insulative material surrounding each of said electrical conductors wherein the insulation material is of sufficient resistivity to prevent electrical breakdown while carrying cardioversion energy, and a tubular lead body possessing the characteristic of preferentially bending about a bending axis, the electrical conductors being carried in such a manner in said tubular lead body that the spacing therebetween is maintained even when said tubular lead body is sharply bent about said bending axis.

8. The catheter electrode of claim 7 wherein said tubular body is oval.

9. A method of electrically connecting a high-energy electrical pulse generator with a heart of a patient via electrodes implanted in, on, or about the heart, the method comprising:

providing an electrode lead having an outer body with at least a first section having a major axis and a minor axis for preferential bending about the major axis, and insulated conductors within the outer body and electrically connected to the electrodes and capable of carrying high-energy levels of current;

implanting the electrodes and electrode lead by passing the electrodes and lead in the patient's body along a path having at least one sharp bend and implanting the electrodes in, on, or about the heart, such that the first section of the lead is positioned along the path at any sharp bend and the first section preferentially bends about the major axis, thereby maintaining the insulated conductors in spaced-apart relation within the first section; and electrically connecting the lead to the high-energy electrical pulse generator for delivering cardioversion or defibrillation pulses when indicated.

10. A method for connecting electrodes implanted in, on, or about the heart of a patient with a source of electrical energy, the method comprising the steps of:

providing a tubular lead body of insulating material housing at least two insulated electrical conductors, said lead body having an elongated cross section throughout a length portion which is implanted within the patient, the cross section having a major axis and a minor axis for preferential bending of the lead body about the major axis substantially to maintain the spacing between said at least two insulated electrical conductors disposed in said lead body along said major axis;

implanting the tubular lead body within the body of a patient between the source of electrical energy and the electrodes, and passing said lead body along a path in the body of the patient having at least one sharp bend so that said preferential bending of the lead body thereby maintains the spacing between the electrical conductors at any sharp bend; and electrically connecting the conductors of said tubular lead body to said electrodes and said source of electrical energy to deliver cardioversion or defibrillation energy to the heart of the patient when indicated.

11. The method of claim 10, wherein said step of implanting comprises the step of passing said lead body between a first rib and the clavicle of the patient.

12. A patient-implanted electrode assembly connected to a pulse generator comprising:

electrical conductors adapted to extend from the pulse generator to the patient's heart, said electrical conductors of sufficient diameter to effectively carry a defibrillation current to the heart; and a tubular lead body of insulating material carrying said electrical conductors and having an elongated cross-sectional shape with a major axis and a minor axis at least at a location where the lead body is to be sharply bent, so as to promote preferential bending of the lead body about a major axis and to prevent the moving together and hence the short circuiting of the conductors, the conductors being free to move within said tubular lead body when the lead body is generally straight, but which are disposed in spaced relation on said major axis when and at locations where the lead body is sharply bent.

13. The electrode assembly of claim 12 wherein the lead body has an oval cross-sectional shape.

14. The electrode assembly of claim 12 wherein the lead body is readily resiliently compressed to form a cylindrical catheter of circular cross section for insertion into the patient.

15. The electrode assembly of claim 12 wherein the major axis width is of the approximate range from 2.0 to 7.0 mm, the minor axis width is of the approximate range from 1.0 to 3.0 mm, and each conductor diameter is of the approximate range from 0.5 to 2.0 mm.

16. An electrical lead for connecting a pulse generator to a patient-implanted electrode for delivering high-energy discharges to the heart of the patient, the lead preventing short circuiting between a pair of insulated electrical conductors in the event the lead is bent sharply, the lead comprising:

a tubular lead body of insulating material having an elongated cross section with a major axis and a minor axis, the lead body preferentially bending about the major axis; and at least two insulated conductors contained within the lead body and disposed in spaced relation along the major axis, without experiencing forces urging together the insulated conductors even at regions where the electrical lead is sharply bent, said insulated conductors having sufficient cross sectional area to carry current for defibrillating a heart.

17. The electrical lead of claim 16 wherein the lead body has an oval cross section.

18. A catheter electrode for association with a remote electrical energy source, and to be implanted within the body of a patient, said catheter electrode comprising at least two conductive defibrillation electrodes for residing in or about the heart of a patient, an electrical conductor associated with each of said conductive electrodes, each of said electrical conductors for carrying levels of current for defibrillating the heart, insulative material surrounding each of said electrical conductors wherein the insulation material is of sufficient resistivity to prevent electrical breakdown while carrying defibrillation energy, and a tubular lead body possessing the characteristic of preferentially bending about a bending axis, the electrical conductors being carried in such a manner in said tubular lead body that the spacing therebetween is maintained even when said tubular lead body is sharply bent about said bending axis.

19. The catheter electrode of claim 18 wherein said tubular body is oval.

* * * * *